United States Patent [19]

Elliott et al.

[11] Patent Number: 5,665,717
[45] Date of Patent: Sep. 9, 1997

[54] CARBACEPHALOSPORIN COMPOUND, THEIR PREPARATION AND USE

[75] Inventors: Richard Leonard Elliott; Neville Hubert Nicholson, both of Betchworth; Andrew Kenneth Takle, Betchwork, all of Great Britain

[73] Assignee: Pfizer Inc., New York, N.Y.

[21] Appl. No.: 522,411

[22] PCT Filed: Mar. 10, 1994

[86] PCT No.: PCT/EP94/00811

§ 371 Date: Jan. 18, 1996

§ 102(e) Date: Jan. 18, 1996

[87] PCT Pub. No.: WO94/21633

PCT Pub. Date: Sep. 29, 1994

[30] Foreign Application Priority Data

Mar. 20, 1993 [GB] United Kingdom ............... 9305837

[51] Int. Cl.[6] .................... A61K 31/395; C07D 221/06
[52] U.S. Cl. ........................................ 514/210; 540/205
[58] Field of Search ........................... 514/210; 540/205

[56] References Cited

U.S. PATENT DOCUMENTS

| | | | |
|---|---|---|---|
| 4,485,110 | 11/1984 | Osborne | 424/270 |
| 4,544,549 | 10/1985 | Harbridge | 424/114 |
| 4,798,828 | 1/1989 | Osborne | 514/192 |
| 5,099,015 | 3/1992 | Hornback et al. | 540/205 |

FOREIGN PATENT DOCUMENTS 494733  7/1992  European Pat. Off. .

OTHER PUBLICATIONS

Greengrass et al., Studies on 1-carbadethiacephems, part III, Tetrahedron Letters, vol.23, No. 23, pp. 2419–2422.
Sato et al., Agric. Biol. Chem., vol. 47, No. 4, pp. 799–806.
Doyle et al., Can. J. Chem., vol. 57, No. 2, pp. 222–226.

Primary Examiner—Joseph McKane
Assistant Examiner—Richard S. Myers, Jr.
Attorney, Agent, or Firm—Ladas & Parry

[57] ABSTRACT

Carbacephalosporin compounds of formula (I),

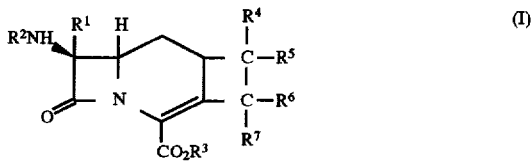

salts thereof, processes for their synthesis and uses thereof, wherein: $R^1$ is hydrogen, methoxy or formamido; $R^2$ is an acyl group; $CO_2R^3$ is a carboxy group or a carboxylate anion, or $R^3$ is a carboxy protecting group or a pharmaceutically acceptable salt-forming group or in vivo hydrolysable ester group; $R^4$, $R^5$, $R^6$ and $R^7$ represent hydrogen or a substituent; $R^4$ and $R^7$ may be replaced by a chemical bond between the two carbon atoms shown; $R^5$ and $R^6$ may be linked together into a cyclic system. The compounds (I) have antibacterial properties.

16 Claims, No Drawings

CARBACEPHALOSPORIN COMPOUND, THEIR PREPARATION AND USE

This application is a filing under 35 U.S.C. 371 of PCT/EP94/00811, filed Mar. 10, 1994.

This invention relates to novel β-lactam compounds, their preparation and their use, and in particular to a novel class of carbacephalosporins. These compounds have antibacterial properties, and are therefore of use in the treatment of bacterial infections in humans and animals caused by a wide range of organisms.

We have now found a particularly advantageous class of polycyclic compounds based upon a carbacephalosporin nucleus.

The present invention provides a carbacephalosporin compound of formula (I) or a salt thereof:

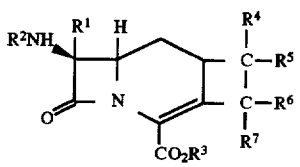

wherein;

$R^1$ is hydrogen, methoxy or formamido;

$R^2$ is an acyl group, in particular that of an antibacterially active cephalosporin;

$CO_2R^3$ is a carboxy group or a carboxylate anion, or $R^3$ is a readily removable vivo hydrolysable ester group;

$R^4$, $R^5$, $R^6$ and $R^7$ independently represent hydrogen or a substituent;
wherein $R^4$ and $R^7$ may be absent and be replaced by a chemical bond between the two carbon atoms shown;

and wherein $R^5$ and $R^6$ may be linked together into a cyclic system of formula:

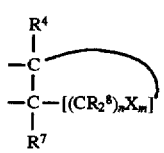

wherein X represents —O— or —$NR^8$—, wherein each $R^8$ may be the same or different and independently represents hydrogen or a substituent, or two groups $R^8$ may be linked into a ring system, or any two adjacent —$CR^8{}_2$— units may be replaced by a —$CR^8$=$CR^8$— unit, and wherein n is an integer 1 to 7, m is 0, 1, 2 or 3.

In compounds of formula (I) wherein $R^1$ is formamido, the formamido group can exist in conformations wherein the hydrogen atoms of the —NH—CHO moiety are cis- or trans-; of these the cis conformation normally predominates.

Since the compounds of the present invention are intended for use as therapeutic agents for antibacterial use in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

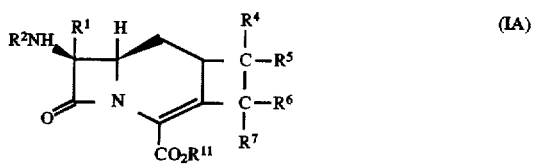

wherein $R^1$, $R^2$, $R^4$, $R^5$, $R^6$, and $R^7$ are as defined with respect to formula (I) and the group $CO_2R^{11}$ is $CO_2R^3$ where $CO_2R^3$ is a carboxy group or a carboxylate anion.

Accordingly, the present invention provides a compound of formula (Ia) or a pharmaceutically acceptable salt or in vivo hydrolysable ester thereof, for use as a therapeutic agent, and in particular an in vivo hydrolysable ester thereof for use as an orally administrable therapeutic agent.

The present invention further provides a compound of formula (Ia) or a pharmaceutically acceptable salt or in vivo hydrolysable ester thereof, for use in the treatment of bacterial infections, more particularly an in vivo hydrolysable ester thereof for use in the oral treatment of bacterial infections.

The present invention also includes a method of treating bacterial infections in humans and animals which comprises the administration of a therapeutically effective mount of an antibiotic compound of the formula (Ia) or a pharmaceutically acceptable in vivo hydrolysable ester thereof, in particular the oral administration of a therapeutically effective amount of an in vivo hydrolysable ester.

In addition, the present invention includes the use of a compound of formula (Ia) or a pharmaceutically acceptable salt or in vivo hydrolysable ester thereof, for the manufacture of a medicament for the treatment of bacterial infections, in particular the use of an in vivo hydrolysable ester for the manufacture of a medicament for the oral treatment of bacterial infections.

Those compounds of the formula (I) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

Also included within the scope of the invention are salts and carboxy-protected derivatives, including in vivo hydrolysable esters, of any carboxy groups that may be present as optional substituents in compounds of formula (I) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus- containing group, an oxime radical of formula —N=$CHR^7$ where $R^7$ is aryl or heterocyclic, or an in vivo hydrolysable ester radical such as defined below.

A carboxyl group may be regenerated from any of the above esters by usual methods appropriate to the particular $R^3$ group, for example, acid- and base-catalysed hydrolysis, or by enzymically-catalysed hydrolysis or by hydrogenolysis under conditions wherein the remainder of the molecule is substantially unaffected.

When used herein the term 'aryl' means phenyl and naphthyl, each optionally substituted with up to five, preferably up to three, groups selected from halogen, mercapto, $(C_{1-6})$alkyl, phenyl, $(C_{1-66})$alkoxy, hydroxy$(C_{1-6})$alkyl, mercapto$(C_{1-6})$alkyl, halo$(C_{1-6})$alkyl, hydroxy, amino, nitro, carboxy, $(C_{1-6})$alkylcarbonyloxy, $(C_{1-6})$alkoxycarbonyl, formyl, or $(C_{1-6})$alkylcarbonyl groups.

The terms 'heterocyclyl' and 'heterocyclic' as used herein mean aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$alkoxy, halo $(C_{1-6})$alkyl, hydroxy, carboxy, carboxy salts, carboxy esters such as $(C_{1-6})$alkoxycarbonyl, $(C_{1-6})$ alkoxycarbonyl$(C_{1-6})$alkyl, aryl, and oxo groups. Each heterocyclic ring suitably has from 4 to 7, preferably 5 or 6, ring atoms. The term 'heteroaryl' refers to heteroaromatic heterocyclic rings. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

The term 'heteroaryl' as used herein means a heteroaromatic heterocyclic ring or ring system, suitably having 5 or 6 ring atoms in each ring.

When used herein the terms 'alkyl', 'alkenyl', 'alkynyl' and 'alkoxy' include straight and branched chain groups containing from 1 to 6 carbon atoms, such as methyl, ethyl, propyl and butyl.

When used herein the term 'halogen' refers to fluorine, chlorine, bromine and iodine.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

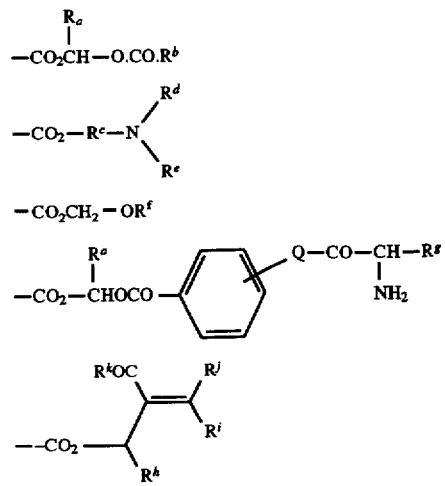

wherein $R^a$ is hydrogen, $(C_{1-6})$alkyl, $(C_{3-7})$cycloalkyl, methyl, or phenyl, $R^b$ is $(C_{1-6})$alkyl, $(C_{1-6})$alkoxy, phenyl, benzyl, $(C_{3-7})$cycloalkyl, $(C_{3-7})$cycloalkyloxy, $(C_{1-6})$alkyl $(C_{3-7})$cycloalkyl, 1-amino $(C_{1-6})$alkyl, or 1-($(C_{1-6})$alkyl) amino $(C_{1-6})$alkyl; or $R^a$ and $R^b$ together form a 1,2-phenylene group optionally substituted by one or two methoxy groups; $R^c$ represents $(C_{1-6})$alkylene optionally substituted with a methyl or ethyl group and $R^d$ and $R^e$ independently represent $(C_{1-6})$alkyl; $R^f$ represents $(C_{1-6})$alkyl; $R^g$ represents hydrogen or phenyl optionally substituted by up to three groups selected from halogen, $(C_{1-6})$alkyl, or $(C_{1-6})$alkoxy; Q is oxygen or NH; $R^h$ is hydrogen or $(C_{1-6})$alkyl; $R^i$ is hydrogen, $(C_{1-6})$alkyl optionally substituted by halogen, $(C_{2-6})$alkenyl, $(C_{1-6})$alkoxycarbonyl, aryl or heteroaryl; or $R^h$ and $R^i$ together form $(C_{1-6})$ alkylene; $R^j$ represents hydrogen, $(C_{1-6})$alkyl or $(C_{1-6})$ alkoxycarbonyl; and $R^k$ represents $(C_{1-8})$alkyl, $(C_{1-8})$ alkoxy, $(C_{1-6})$ alkoxy$((C_{1-6}))$alkoxy or aryl.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl) but-2-enyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

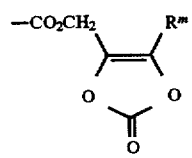

wherein $R^m$ is hydrogen, $(C_{1-6})$alkyl or phenyl.

A preferred in vivo hydrolysable ester group is the pivaloyloxymethyl ester.

Suitable pharmaceutically acceptable salts of the carboxy group of the compound of formula (I) include metal salts, eg aluminium, alkali metal salts such as sodium or potassium, especially sodium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)- amine, cycloalkylamines such as dicyclohexylamine, or with procaine, dibenzylamine, N,N-dibenzylethylene-diamine, 1-ephenamine, N-methylmorpholine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins. Other useful salts include the lithium salt and silver salt. Salts of formula (I) may be prepared by salt exchange in conventional manner.

Advantageously, $R^1$ is hydrogen.

Suitable acyl groups R² include those of formulae (a)–(f):

$A_1(CH_2)_p—CH—(CH_2)_m—CO—$  (a)
  |
  $X_1$ $A_2CO—$  (b)

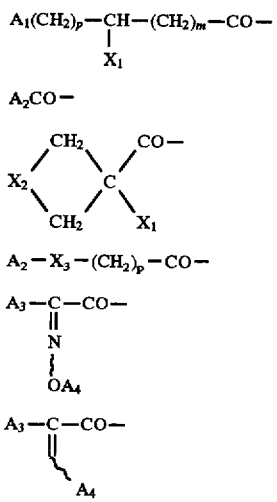  (c)

$A_2—X_3—(CH_2)_p—CO—$  (d)

$A_3—C—CO—$  (e)
   ‖
   N
   |
   $OA_4$ $A_3—C—CO—$  (f)
   ‖
   $A_4$ wherein p is 0, 1 or 2; m is 0, 1 or 2; $A_1$ is $(C_{1-6})$alkyl, substituted $(C_{1-6})$alkyl wherein the substituents may be as for $R^4$ above, $(C_{3-6})$cycloalkyl, cyclohexenyl, cyclohexadienyl, an aryl (including heteroaryl) group, such as phenyl, substituted phenyl, thienyl, pyridyl, or an optionally substituted thiazolyl group, a $(C_{1-6})$ akylthio group or $(C_{1-6})$alkyloxy; $X_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aryl group, for example a phenyl, 2,6-dimethoxyphenyl, 2-alkoxy-1-naphthyl, 3-arylisoxazolyl, or a 3-aryl-5-methylisoxazolyl group, such as 3-(2-chloro-6-fluorophenyl)-5-methylisoxazol-4-yl;

a substituted alkyl group; or a substituted dithietane; $X_2$ is a —$CH_2OCH_2$—, —$CH_2SCH_2$— or alkylene group; $X_3$ is an oxygen or sulphur atom; $A_3$ is an aryl or heteroaryl group such as phenyl, substituted phenyl, furyl, aminothiazolyl or aminothiadiazolyl in which the amino group is optionally protected; and $A_4$ is hydrogen, $(C_{1-6})$alkyl, $(C_{3-8})$cycloalkyl, $(C_{3-8})$ cycloalkyl$(C_{1-6})$alkyl, $(C_{1-6})$ alkoxycarbonyl$(C_{1-6})$ alkyl, $(C_{2-6})$alkenyl, carboxy$(C_{1-6})$alkyl, $(C_{2-6})$ alkynyl, aryl or $(C_{1-6})$alkyl substituted by up to three aryl groups.

Suitably when R² is a group (a), $A_1$ is $(C_{1-6})$alkyl, $(C_{3-6})$cycloalkyl, cyclohexenyl, cyclohexadienyl, phenyl, substituted phenyl (eg substituted as for "aryl" above) such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Suitably when R² is a group of formula (d), $A_2$ is phenyl, $X_3$ is oxygen and p is 0.

Alternatively when R² is a group of formula (e) or (f) suitable values for the group $A_3$ include those commonly found in antibacterially active cephalosporins containing a hydroxyimino, substituted hydroxyimino or vinyl group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, fur-2-yl, thien-2-yl, 2-(2-chloroacetamido)thiazol-4-yl, 2-tritylamino-thiazol-4-yl, 5-amino- 1,2,4-thiadiazol-3-yl and 4-aminopyrimid-2-yl.

In compounds of formula (Ia) a preferred acyl group R² is one of formula (e), having a group, $A_3$ which is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (Ia) include methyl and hydrogen.

Suitably the group $R^2NH$ may be a 2-(2-aminothiazol-4-yl)-2-(Z)-methoxy- or hydroxy-iminoacetamido group, in which the amino group may be in a protected form.

It will be appreciated that compounds of the invention wherein R² is a group of formula (e) (or (f)) can exist as syn and anti (or E and Z) isomers or mixtures thereof. Both isomers are encompassed within the scope of this invention.

Preferably the compounds of the invention wherein R² is a group of formula (e) have the syn configuration (i.e. have the group $OA_4$ syn to the amide linkage) or are enriched in that isomer.

Similarly, when R² is a group of formula (f), the group $A_4$ is preferably cis to the amide linkage, i.e. when group (f) is 2-amino-thiazol-4-yl, the Z-configuration is preferred.

When one or more of $R^4$, $R^5$, $R^6$ and $R^7$ represent substituent groups they may suitably be selected from alkyl, alkenyl, alkynyl, alkoxy, hydroxy, thioalkyl, thioaryl, halogen, amino, cyano, alkylamino, acylamino, dialkylamino, $CO_2R$, $CONR_2$, $SO2NR^2$(where R is hydrogen or $(C_{1-6})$alkyl), aryl, heterocyclyl, $(C_{1-6})$ alkanoyl, $(C_{1-6})$alkoxycarbonyl, $(C_{1-6})$alkoxy $(C_{1-6})$alkyl, $(C_{1-6})$ alkanoyloxy, $(C_{1-6})$alkanoyloxy $(C_{1-6})$alkyl, and trialkylsilyl and where any $R^4$, $R^5$, $R^6$ or $R^7$ alkyl substituent may be substituted with any other of the aforementioned groups. Examples of such groups include methyl, butyl, ethoxy, phenyl, hydroxymethyl, acetyl, thiophenyl, methoxymethyl, carbonyloxymethyl and trimethylsilyl. Suitably one, two, three or four of $R^4$, $R^5$, $R^6$ and $R^7$ may be hydrogen, for example both $R^6$ and $R^7$ may be hydrogen, and one of $R^4$ or $R^5$ may be hydrogen.

The compound of formula (I) may suitably have a part formula (IBi) or (IBii):

  (IBi)

  (IBii)

where one or both of $R^4$ and $R^5$ may be substituent groups other than hydrogen.

When $R^5$ and $R^6$ are linked together into a cyclic system $R^4$ and $R^7$ may suitably be hydrogen, and the ring system may suitably be a 5- or 6-membered ring system of part formula (IBiii), (IBiv) or (IBv) or (IBvi):

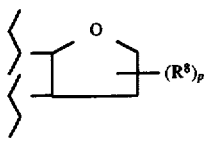 (IBiii)

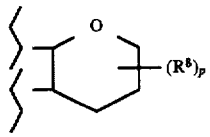 (IBiv)

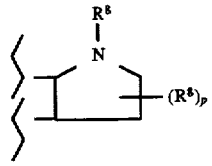 (IBv)

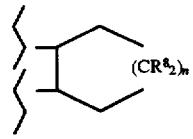 (IBvi)

where $R^8$ and n are as defined in formula (I) above and p is zero or an integer up to the number of carbon atoms in the ring.

When $R^8$ represents a substituent group on a ring carbon atom it may be hydrogen or independently selected from the same list of substituents from which $R^4$, $R^5$, $R^6$ and $R^7$ may be selected, and suitably such an $R^8$ may be hydrogen. When $R^8$ represents a substituent on a ring nitrogen atom it may be hydrogen, $(C_{1-6})$alkyl, or an amino substituting or protecting group such as acyl.

Suitably in part formulae (IBiii–IBvi) $R^8$ may be hydrogen, and n may be 1 or 2.

When two groups $R^8$ are linked together to form a ring system, such a ring system may be an aliphatic ring system, for example a cycloalkane or cycloalkene ring system, having from 3 to 7 ring carbon atoms. Such an aliphatic ring system may optionally be substituted by one or more substituents independently selected from the same list of substituents from which $R^4$, $R^5$, $R^6$ and $R^7$ may be selected. The ring system any alternatively by an aryl or heterocyclyl ring system as defined above. Two groups $R^8$ may be linked together for example to form an optionally substituted phenyl ring system, for example in a compound of part formula (IBvii):

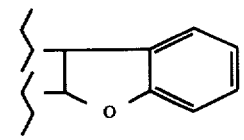 (IBvii)

wherein the phenyl ring shown in (IBvii) may be substituted with one or more substituents.

In the compounds of part formula (IBi-vii) above the ring systems may exist in a number of isomeric forms including stereoisomers, and the present inventions includes all of them as well as mixtures thereof.

Certain compounds of the invention include an amino group which may be substituted and/or protected. Suitable amino substituting and protecting groups are those well known in the art which may be removed under conventional conditions without disruption of the remainder of the molecule.

Examples of amino substituting and protecting groups include $(C_{1-6})$ alkanoyl; benzoyl; benzyl optionally substituted in the phenyl ring by one or two substituents selected from $(C_{1-4})$alkyl, $(C_{1-4})$alkoxy, trifluoromethyl, halogen, or nitro; $(C_{1-4})$alkoxycarbonyl; benzyloxycarbonyl or trityl (ie triphenylmethyl) substituted as for benzyl above; allyloxycarbonyl, trichloroethoxycarbonyl or chloroacetyl.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure, particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) include the pharmaceutically acceptable carboxylic acid below, and salts and in-vivo hydrolysable esters thereof.

(4S,8R,9S,11R,12S)- 12-[2-(2-aminothiazol-4-yl)-2-(Z)-methoxyiminoacetamido]-13-oxo-1-aza-6,7-benzotetracyclo [9.2.0.0$^{3,9}$.0$^{4,8}$]trideca-2,6-diene-2-carboxylic acid The present invention provides a process for the preparation of a compound of formula (I) or (Ia) as defined above in which —$CO_2R^3$ is a carboxy group or carboxylate anion or $R^3$ is a pharmaceutically acceptable salt-forming group or in-vivo hydrolysable ester group, wherein a compound of formula (I) as defined above in which $R^3$ is a carboxy protecting group has its group $CO_2R^3$ replaced by a group $CO_2R^3$ which is a carboxy group or a carboxylate anion, or in which $R^3$ is a pharmaceutically acceptable salt-forming group or in-vivo hydrolysable ester group.

The present invention further provides a process for the preparation of a compound of formula (I), which process comprises treating a compound of formula (II) or a salt thereof:

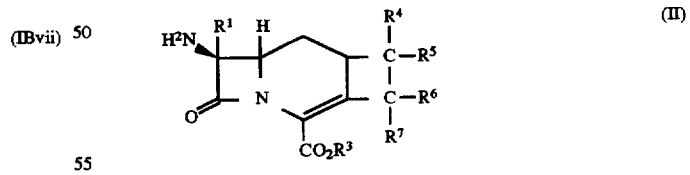 (II)

wherein $R^1$, $CO_2R^3$, $R^4$, $R^5$, $R^6$, and $R^7$ are as hereinbefore defined, wherein any reactive groups may be protected, and wherein the amino group is optionally substituted with a group which permits acylation to take place; with an acid of formula (III) or a N-acylating derivative thereof:

$R^2OH$ (III)

wherein $R^2$ is the acyl group as defined with respect to formula (I) and wherein any reactive groups may be protected; and thereafter, if necessary or desired, carrying out one or more of the following steps:

i) removing any protecting groups;
ii) converting the group $CO_2R^3$ into a different group $CO_2R^3$;
iii) converting the group $R^2$ into a different group $R^2$;
iv) converting the sulphur atom into an oxidised sulphur atom;
v) converting the product into a salt or ester.

Acids of formula (III) may be prepared by methods known in the art, or methods analogous to such processes. Suitable processes include those described, for example, in UK Patent 2 107 307 B, UK Patent Specification No. 1,536,281, and U.K. Patent Specification No. 1,508,064.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula $—P.R^7R^8$ wherein $R^7$ is an alkyl, haloalkyl, aryl, aralkyl, alkoxy, haloalkyl, aryl, aralkyl, alkoxy, haloalkoxy, aryloxy, aralkyloxy or dialkylamino group, $R^8$ is the same as $R^7$ or is halogen or $R^7$ and $R^8$ together form a ring; suitable such phosphorus groups being $—P(OC_2H_5)_2$, $—P(C_2H_5)2$,

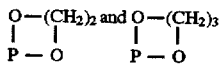

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis-(trimethylsilyl) acetamide, N,O-bis(trimethylsilyl)-trifluoroacetamide, N-methyl-N-trimethylsilylacetamide, N-methyl-N-trimethylsilyl-trifluoroacetamide, N,N'-bis(trimethylsilyl) urea, and N,O-bis(trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30° –60° C., preferably 40° –50° C.

The above process may optionally be carried out in the presence of a small quantity, for example 0.1 equivalents, of a silyl halide, for example a tri($C_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide or alternatively a symmetrical or mixed anhydride. The acylation may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a ($C_{1-6}$)-1,2-alkylene oxide—such as ethylene oxide or propylene oxide. The acylation reaction using an acid halide may be carried out at a temperature in the range –50° C. to +50° C., preferably –20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate. The acylation with acid halide or anhydride is suitably carried out in the presence of a basic catalyst such as pyridine or 2,6-lutidine.

Acid halides may be prepared by reacting the acid (III) or a salt or a reactive derivative thereof with a halogenating (eg chlorinating or brominating) agent such as phosphorus pentachloride, thionyl chloride, oxalyl chloride or phosgene.

Suitable mixed anhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid).

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexyl-carbodiimide, or N-ethyl-N'-[3-(dimethylamino)propyl]-carbodiimide; a suitable carbonyl compound, for example, N,N'-carbonyldiimidazole or N,N'-carbonyldi-triazole; an isoxazolinium salt, for example, N-ethyl-5-phenylisoxazolinium-3-sulphonate or N-t-butyl-5- methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$-$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at –40° to +30° C., if desired in the presence of an acid binding agent such as pyridine. A catalyst such as 4-dimethylaminopyridine may optionally also be added. A preferred solvent for the above acylation reaction is dichloromethane.

The optional removal of protecting group (i), the optional conversion of $CO_2R^3$ (ii), the optional conversion (iii) of $R^2$ to a different $R^2$, $CO_2R^3$ to a different $CO_2R^3$ and (iv), oxidation of the sulphur, and (v) the optional formation of a salt or ester, may be carried out using methods well known in the art of cephalosporin and penicillin chemistry.

For example, the sulphur atom may be oxidised by methods of oxidation or reduction well known in the art of cephalosporin and penicillin synthesis, as described, for example, in European Patent Application Publication No. 0 114 752. For example, sulphoxides may be prepared from the corresponding sulphide by oxidation of the sulphur atom with a suitable oxidising agent, for example an organic peracid such as m-chloroperbenzoic acid.

A reduction step is generally effected by processes well known in the art of β-lactam chemistry, for example using phosphorus trichloride in dimethylformamide.

For example, removal of protecting groups may be carried out by any convenient method known in the art such that unwanted side reactions are minimised. When for example $R^3$ is the protecting group p-methoxybenzyl, this group may suitably be removed by treatment of the protected compound with aluminium chloride in the presence of anisole. Separation of unwanted by-products may be carried out using standard methods.

Compounds of formula (II) may be prepared from compounds of formula (IV):

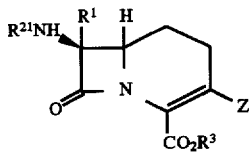

wherein $R^1$ and $R^3$ are as defined in formula (I), $R^{21}$ is a group $R^2$ as hereinbefore defined or is an amino-protecting group or is hydrogen or a group which permits N-acylation to take place and Z is a nucleophilic leaving group, by reaction with a compound of formula (V):

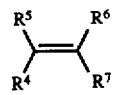

wherein $R^4$, $R^5$, $R^6$ and $R^7$ are as defined with reference to formula (I), $R^4$ and $R^7$ may be absent and be replaced by a bond to form an alkyne, and wherein $R^5$ and $R^6$ may be linked together into a cyclic system of formula:

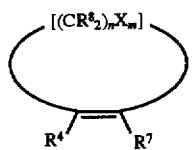

wherein X, $R^8$, n and m are as defined with respect to formula (I) above.

In formula (IV) a suitable group Z is a trifluoromethyl sulphonyloxy or fluorosulphonyloxy group. A suitable group $R^{21}$ is phenylacetyl. A suitable group $R^3$ is p-methoxybenzyl. A suitable group $R^1$ is hydrogen.

When in the compound of formula (V) $R^4$ and $R^7$ are replaced by a bond between the carbon atoms, the compound of formula (V) is an alkyne, and by the use of such an alkyne compounds of formula (I) may be formed in which a cyclobutene group is present, eg (IBii) above.

Suitable values for $R^4$, $R^5$, $R^6$, $R^7$, $R^8$, X, m and n in the compound of formula (V) are as defined for formulae (IBi to viii) above.

Compounds of formula (V) are known, for example, alkylvinyl ethers, dihydrofurans, dihydropyrans, vinylalkanoates, pyrrolines, tetrahydropyridines, alkenes, alkynes, benzofurans, cycloalkenes, indenes, etc, and suitable compounds of formula (V) to form a particular compound of formula (II) will be apparent to those skilled in the art.

The reaction between compounds of formula (IV) and (V) may be carried out in a solvent suitably an organic solvent such as dichloromethane, and in the presence of a base, suitably an organic amine such as 1,8-diazabicyclo [5.4.0] undec-7-ene ("DBU"), at a temperature between +40° C. and −40° C. such as at 0° C. The reaction is facile and may occur simply on stirring the reagents together.

The reaction between a compound of formula (IV) and formula (V) to form a compound of formula (II) is novel, and is a further aspect of this invention.

Compounds of formula (IV) may be prepared from compounds of formula (VI):

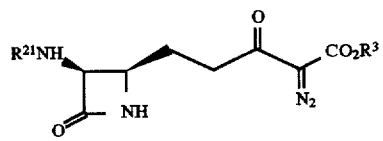

where $R^{21}NH$ and $R^3$ are as defined above, by reflux with a rhodium (II) catalyst, followed by cooling and sequential treatment with a base such as N,N-diisopropylethylamine then trifluoromethanesulphonic anhydride.

Compounds of formula (VI) may be prepared from compounds of formula (VII):

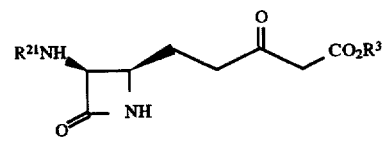

where $R^{21}NH$ and $R^3$ are as defined above, by reaction of the compound (VII) with azide, such as 4-toluenesulphonyl azide in the presence of a base such as N,N-diisopropylethylamine.

Compounds of formula (VII) may be prepared from compounds of formula (VIII):

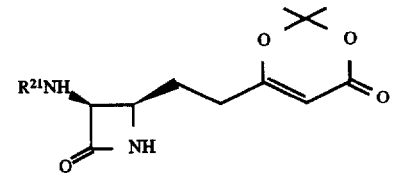

by reaction of the compound (VIII) with an alcohol $R^3OH$, such as p-methoxybenzyl alcohol, for example under reflux.

Compounds of formula (VIII) may for example be prepared by hydrogenation, eg using Pd/C and hydrogen, of compounds of formula (IX):

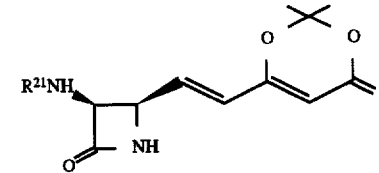

where $R^{21}NH$ is as defined above and the amino group in the azetidinone ring may optionally be protected by a protecting group as described above, which may be removed as described above to yield the compound of formula (VIII).

Compounds of formula (IX) may be prepared from compounds of formula (X):

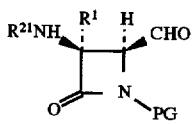

(X)

where $R^1$ and $R^{21}$ are as defined above and PG is an amino protecting group by reaction with known (Oppi Briefs (1990), 22:1, p109–111, C. Bodurow et al) 2,2-(dimethyl)-6-[(triphenylphosphoranylidene)methyl]-4H- 1,3-dioxin-4-one:

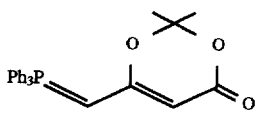

Compounds of formula (X) may for example be prepared from compounds of formula (XI):

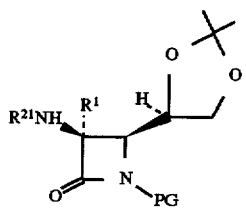

(XI)

where $R^1$, $R^{21}$NH and PG are as defined above by reaction with periodic acid in a suitable solvent such as a tetrahydrofuran/water mixture.

Compounds of formula (XI) may for example be prepared from compounds of formula (XII):

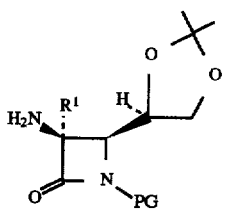

(XII)

where $R^1$ and PG are as defined above, by reaction with an acid of formula $R^{21}$ COOH or an acylating derivative thereof such as an acyl chloride, for example phenylacetyl chloride.

Compounds of formula (XII) may for example be prepared from the known compound L-(S)-glyceraldehyde acetonide (XIII):

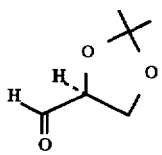

(XIII)

which may be prepared as described in C. Hubschwerlen "Synthesis" (1986), (962), by treatment of (XIII) with p-anisidine for example in a solvent such as dichloromethane to form a compound of formula (XIV):

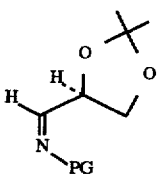

(XIV)

where PG is a protecting group as defined above. The compound of formula (XIV) may then be cyclised to form the azetidinone (XV):

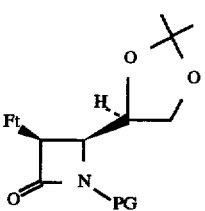

(XV)

where Ft represents phthlalimido, by reaction of the compound of formula (XIV) with phthalimidoacetyl chloride. The phthalimido group Ft may be removed and replaced by an amino group in a compound of formula (XII) by treatment of the compound (XV) with methylhydrazine.

The present invention also provides a pharmaceutical composition which comprises a compound of formula (Ia) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No unacceptable toxicological effects are expected when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a β-lactamase inhibitor may be employed.

Advantageously, the compositions also comprise a compound of formula (XVI) or a pharmaceutically acceptable salt or ester thereof:

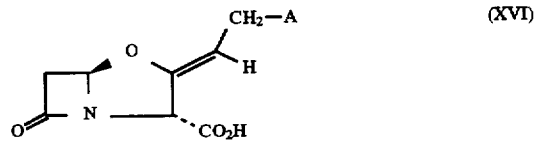

wherein

A is hydroxyl, substituted hydroxyl, thiol, substituted thiol, amino, mono- or di-hydrocarbyl-substituted amino, or mono- or di-acylamino; an optionally substituted triazolyl group; or an optionally substituted tetrazolyl group as described in EP-A-0 053 893.

A further advantageous composition comprises a compound of formula (Ia) or a pharmaceutically acceptable salt or in vivo hydrolysable ester thereof together with a compound of formula (XVII) or a pharmaceutically acceptable salt or in vivo hydrolysable ester thereof:

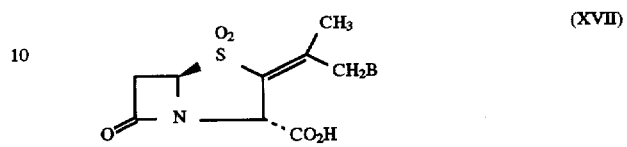

wherein

B represents hydrogen, halogen or a group of formula:

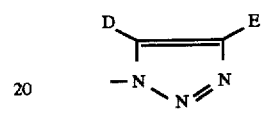

in which D and E are the same or different and each represents hydrogen, (C$_{1-6}$) alkoxycarbonyl or carboxy, or a pharmaceutically acceptable salt thereof.

Further suitable β-lactamase inhibitors include 6-alkylidene penems of formula (XVIII):

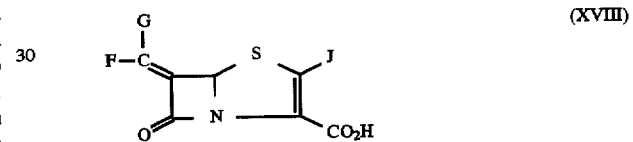

or a pharmaceutically acceptable salt or in vivo hydrolysable ester thereof, wherein F and G are the same or different and each represents hydrogen, or a (C$_{1-10}$) hydrocarbon or heterocyclic group optionally substituted with a functional group; and J represents hydrogen or a group of formula K or -K where K is an optionally substituted (C$_{1-10}$) hydrocarbon or heterocyclic group, as described in EP-A-0 041 768.

Further suitable β-lactamase inhibitors include 6β-bromopenicillanic acid and pharmaceutically acceptable salts and in vivo hydrolysable esters thereof and 6β-iodopenicillanic acid and pharmaceutically acceptable salts and in vivo hydrolysable esters thereof described in, for example, EP-A-0 041 768 and EP-A-0 154 132 (both Beecham Group).

Such compositions of this invention which include a β-lactamase inhibitory amount of a β-lactamase inhibitor are formulated in a conventional manner using techniques and procedures per se known in the art.

The antibiotic compounds of the present invention are active against a wide range of organisms including both Gram-negative organisms such as E. coli and Gram-positive organisms such as S. aureus.

The following Examples illustrate the preparation of compounds of the invention and intermediates thereto.

Preparation 1

4-Methoxybenzyl(6R,7S)-7-phenylacetamido-3-(trifluoromethylsulphonyloxy)-1-carba-1-dethiaceph-3-em-4-carboxylate.

1a) (3S,4S)-4-[(R)-2,2-Dimethyl-1,3-dioxolon-4-yl]-1-(4-methoxyphenyl)-3-phthalimidoazetidin-2-one A crude aqueous solution of L-(S)-glyceraldehyde acetonide (obtained from 0.15 mol of 5,6-isopropylidene- L-gulono-1,4-lactone, C. Hubschweden, Synthesis, 1986, 962) was treated with a solution of p-anisidine (16.2g, 0.13 mol) in dichloromethane (300 ml). The reaction mixture was stirred overnight at room temperature, then the organic phase separated and the aqueous phase extracted twice with dichloromethane (100 ml). The combined organic layers were dried over magnesium sulphate, filtered and reduced in volume to ~200 ml. The crude imine was treated with triethylamine (26.7 ml, 0.19 mol) and cooled to −30° C. A solution of phthalimidoacetyl chloride (42.8 g, 0.19 mol) in dichloromethane (150 ml) was added dropwise over 45 min. After stirring for 2.5 h at room temperature, the reaction mixture was filtered, and the filtrate washed successively with water (×3), 1M hydrochloric acid, saturated aqueous sodium hydrogen carbonate solution, water and brine. The organic phase was dried over magnesium sulphate, filtered and concentrated in vacuo. The residue was passed through a short column of silica eluting with dichloromethane, concentrated, and the residue purified by crystallisation from ethyl acetate/hexane. The title compound as obtained as a yellow solid (23.78 g, 44%); m.p. 164–166° C.; $[\alpha]_D$+55.0° (c 1.00 CHCl$_3$); (Found: C, 65.44; H, 5.27;N, 6.75%; M$^+$422.1487. C$_{23}$H$_{22}$N$_2$O$_6$ requires C, 65.40; H, 5.25; N, 6.63%; M 422.1478.); $v_{max}$ (CH$_2$Cl$_2$) 1760, 1724, 1514, 1384, 1265 and 1247cm$^{-1}$; $\delta_H$ (CDCl$_3$) 1.27 (3H, s), 1.50 (3H, s), 3.53 (1H, dd, J 8.4, 6.5 Hz), 3.75 (1H, dd, J 8.4, 6.5 Hz), 3.82 (3H, s), 4.42–4.57 (2H,m), 5.53 (1H, d, J 5.4 Hz), 6.91 (2H, d, J 9.1 Hz), 7.74 (2H, d, J 9.1 Hz), 7.70–7.84 (2H, m) and 7.89–7.95 (2H, m).

1b) (3S,4S)-3 Amino-4-[(R)-2,2-dimethyl-1,3-dioxolon-4-yl]-1-(4-methoxyphenyl)azetidin-2-one Methyl hydrazine (8.1 ml, 152.3 mmol) was added to a solution of (3S,4S)-4-[(R)-2,2-dimethyl-1,3-dioxolan-4-yl]-1-(4-methoxyphenyl)-3-phthalimidoazetidin-2-one (23.78 g, 56.4mmol) in dichloromethane (230 ml). The reaction mixture was heated at reflux for 6 h and then stirred overnight at room temperature. The precipitated solid was filtered off through celite and the filtrate washed successively with saturated aqueous sodium hydrogen carbonate solution and brine. After drying over magnesium sulphate, the solvent was evaporated in vacuo to yield a pale yellow solid. Recrystallisation from dichloromethane/hexane yielded the title compound as a white solid (12.26 g, 74%); m.p. 163°–165° C.; $[\alpha]_D$−98.5° (c 1.00 MeOH); (Found: M$^+$292.1428. C$_{15}$H$_{20}$N$_2$O$_4$ requires M 292.1423); $v_{max}$ (CH$_2$Cl$_2$) 1744, 1513 and 1270cm$^{-1}$; $\delta_H$ (CDCl$_3$) 1.35 (3H, s), 1.43 (3H, s), 1.70 (2H, br.s, exch.), 3.79 (3H, s), 3.85 (1H, m), 4.20 (1H, m), 4.27–4.38 (3H, m), 6.86 (2H, d, J 9.0 Hz) and 7.55 (2H, d, J 9.0 Hz).

1c) (3S,4S)-4-[(R)-2,2-Dimethyl-1,3-dioxolan-4-yl]-1-(4-methoxyphenyl)-3-phenylacetamidoazetidin-2-one A solution of (3S,4S)-3-amino-4-[(R)-2,2-dimethyl-1,3-dioxolan-4-yl]-1-(4-methoxyphenyl)azetidin-2-one (12.21 g, 41.8 mmol) in dichloromethane (160 ml) was cooled to 0° C. and treated sequentially with phenylacetyl chloride (6.1 ml, 46.1 mmol), then triethylamine (6.4 ml, 45.9 mmol). After stirring at 0° C. for 15 min., the mixture was warmed to room temperature and stirred for a further 30 min. The reaction mixture was diluted with dichloromethane and washed twice with water, then brine. The organic layer was dried over magnesium sulphate, filtered and the solvent evaporated in vacuo to yield a solid. Trituration with diethyl ether yielded the title compound (16.16 g, 94%) as a white amorphous solid; $[\alpha]_D$0.0° (c=1.00 DMF); $v_{max}$ (KBr) 1757, 1661 and 1510 cm$^{-1}$; $\delta_H$ (CDCl$_3$) 1.16 (3H, s), 1.25 (3H, s), 3.62 (2H, s), 3.69–3.82 (2H, m), 3.76 (3H; s), 4.02 (1H, m), 4.36 (1H, dd, J 5.5, 4.0 Hz), 5.58 (1H, dd, J 9.4, 5.5 Hz), 6.56 (1H, d, J 9.4 Hz), 6.83 (2H, d, J 8.9 Hz) and 7.25–7.40 (7H, m); m/z (EI) 410 (5); (CI, +ve ion, ammonia) 411 (MH$^+$).

1d) (3S,4S)-4-Formyl-1-(4-methoxyphenyl)-3-phenylacetamidoazetidin-2-one

Periodic acid (18.7 g, 45.6mmol) was added to a suspension of (3S,4S)-4-[(R)-2,2-dimethyl-1,3-dioxolan-4-yl]-1-(4-methoxyphenyl)-3-phenylacetamidoazetidin-2-one (15.1 g, 36.8mmol) in tetrahydrofuran (210 ml) and water (210 ml). The reaction mixture was heated under reflux for 1.5 h and then cooled in ice. The precipitated product was collected by filtration, washed with water and dried over phosphorus pentoxide to yield the title compound as a mixture of aldehyde and the corresponding hydrate (10.18 g, 82%); $v_{max}$ (KBr) 1713, 1638, 1552 and 1514cm$^{-1}$; aldehyde $\delta_H$ (d$_6$-DMSO) 3.43 and 3.50 (2H, ABq, J 14.4 Hz), 3.73 (3H, s), 4.95 (1H, dd, J 6.1, 1.2 Hz), 5.19 (1H, m), 6.95 (2H, d, J 9.0 Hz), 7.18–7.35 (7H, m), 9.09 (1H, d, J 7.3 Hz) and 9.52 (1H, d, J 1.2 Hz); hydrate $\delta_H$ (d$_6$-DMSO) 3.50 (2H, s), 3.72 (3H, s), 4.16 (1H, t, J 5.6 Hz), 5.07 (1H, q, J 5.8 Hz), 5.29 (1H, dd, J 9.4, 5.6 Hz), 6.28 (2H, t, J 6.7 Hz, exch.), 6.9 (2H, d, J 9.1 Hz), 7.19–7.35 (5H, m), 7.52 (2H, J 9.1 Hz) and 8.52 (1H, d, J 9.4 Hz); m/z (EI) 338 (10); (CI, +ve ion, ammonia) 339 (MH$^{+}$, 356 (MNH$_3^+$).

1e) (3S,4R)-4-[(2,2-Dimethyl-4H-1,3-dioxin-4-on-6-yl)ethenyl]-1-(4-methoxyphenyl)-3-phenylacetamidoazetidin-2-one A suspension of (3S,4S)-4-formyl-1-(4-methoxyphenyl)-3-phenyl-acetamidoazetidin-2-one (10.18 g, 30.1 mmol) in acetonitrile (450 ml) was treated with 2,2-(dimethyl)-6-[(triphenylphosphoranylidene)methyl]-4H-1,3-dioxin-4-one (12.5 g, 31.1mmol) and stirred at room temperature for 3 days. The reaction mixture was concentrated in vacuo and the residue purified by flash chromatography on silica gel eluting with ethyl acetate to yield the title compound as a yellow foam (12.40 g, 89%); $[\alpha]_D$−127.5° (c 1.0 CHCl$_3$); $v_{max}$ (CH$_2$Cl$_2$) 3416, 1756, 1724, 1683 and 1513 cm$^{-1}$; $\delta_H$ (CDCl$_3$) 1.72 (3H, s), 1.73 (3H, s), 3.59 (2H, s), 3.77 (3H, s), 4.88 (1H, dd, J 6.0, 5.4 Hz), 5.27 (1H, s), 5.44 (1H, dd, J 7.8, 5.4 Hz), 6.02 (1H, d, J 15.8 Hz), 6.17 (1H, d, J7.8 Hz), 6.42 (1H, dd, J 15.8, 6.1 Hz), 6.83 (2H, d, J 9.0 Hz) and 7.17–7.33 (7H, m); m/z (FAB, +ve ion, 3-nitrobenzyl alcohol/sodium acetate) 485(MN$\alpha^+$).

1f) (3S,4R)-4-[(2,2-Dimethyl-4H-1,3-dioxin-4-on-6-yl)ethyl]-1-(4-methoxyphenyl)-3-phenylacetamidoazetidin-2-one A solution of (3S,4R)-4-[(2,2-dimethyl)-4H-1,3-dioxin-4-on-6-yl)ethenyl]-1-(4-methoxyphenyl)-3-phenylacetamidoazetidin-2-one (12.4 g, 26.8 mmol) in tetrahydrofuran (250 ml) was hydrogenated over 10% palladium on carbon (1.2 g) for 3 h. After filtration through a pad of celite, the filtrate was concentrated to yield the title compound (12.07 g, 97%); $v_{max}$(CH$_2$Cl$_2$) 3416, 1747, 1726, 1684 and 1514cm$^{-1}$; $\delta_H$ (CDCl$_3$) 1.67 (3H, s), 1.68 (3H, s), 2.02–2.15 (4H, m), 3.63 (2H, s), 3.77 (3H, s), 4.21 (1H, m), 5.13 (1H, s), 5.35 (1H, dd, J 7.6, 5.0 Hz), 6.77 (1H, d, J 7.6 Hz), 6.81 (2H, d, J 9.0 Hz), 7.19 (2H, d, J 9.0 Hz) and 7.23–7.40 (5H, m); m/z (FAB, +ve ion, 3-nitrobenzyl alcohol/sodium acetate) 487 (MN$\alpha^+$).

1g) (3S,4R)-4-[(2,2-Dimethyl-4H-1,3-dioxin-4-on-6-yl)ethyl]-3-phenylacetamidoazetidin-2-one A suspension of (3S,4R)-4-[(2,2-dimethyl-4H-1,3-dioxin-4-on-6-yl)ethyl]-1-(4-methoxyphenyl)-3-phenylacetamidoazetidin-2-one (10.58 g, 22.80mmol) in tetrahydrofuran (425 ml) was treated with a solution of ceric ammonium nitrate (40.0 g, 73.0 mmol) in water (245 ml) at 0° C. After stirring for 10 min. at 0° C., the reaction mixture was diluted with ethyl acetate and the aqueous phase extracted four times with a mixture of tetrahydrofuran and ethyl acetate (2:1). The combined organic extracts were washed successively with 5% aqueous sodium hydrogen carbonate solution, 10% aqueous sodium sulphite solution (×3), 5% aqueous sodium hydrogen carbonate solution, water and then brine. After drying over magnesium sulphate, the solvent was evaporated in vacuo to yield the crude title compound (7.50 g, 92%); $v_{max}$ (CH$_2$Cl$_2$) 3410, 1771, 1725, 1684, 1636 and 1512cm$^{-1}$; $\delta_H$ (CDCl$_3$) 1.62–1.75 (2H, m), 1.65 (6H, s), 2.12–2.21 (2H, m), 3.95 (2H, s), 3.80 (1H, m), 5.05 (1H, br.s, exch.), 5.25 (1H, m), 5.29 (1H, s), 6.78 (1H, d, J 7.9 Hz) and 7.21–7.38 (5H, m); m/z (FAB, –ve ion, thioglycerol) 357 (M-H)$^-$.

1h) 4-Methoxybenzyl 3-oxo-5-[(3S,4R)-3-phenylacetamidoazetidin-2-on-4-yl]pentanoate A solution of 4-methoxybenzyl alcohol (1.50 g, 10.87 mmol) in toluene (6 ml) was added to a solution of (3S,14R)-4-[(2,2-dimethyl-4H-1,3-dioxin-4-on-6-yl)ethyl]-3-phenylacetamidoazetidin-2-one (3.86 g, 10.78 mmol) and heated to reflux for 1.5 h. The reaction mixture was concentrated in vacuo and the residue triturated with toluene to give the title compound (3.50 g, 75%) as a crude product; $v_{max}$(CH$_2$Cl$_2$) 3412, 1772, 1747, 1717, 1684 and 1514cm$^{-1}$; $\delta_H$ (CDCl$_3$) 1.63 (2H, m), 2.39 (2H, t, J 7.0 Hz), 3.37 (2H, s), 3.58 (2H, s), 3.68 (1H, m), 3.81 (3H, s), 5.09 (2H, s), 5.18 (1H, m), 6.26 (1H, br.s, exch.), 6.63 (1H, d, J 7.9 Hz), 6.89 (2H, d, J 8.6 Hz) and 7.21–7.38 (7H, m); m/z (FAB, –ve ion, thioglycerol) 437 (M-H)$^-$.

1i) 4-Methoxybenzyl 2-diaza-3-oxo-5-[(3S,4R)-3-phenylacetamidoazetidin-2-on-4-yl]pentanoate A solution of 4-methoxybenzyl 3-oxo[(3S,4R)-3-phenylacetamidoazetidin-2-on-4-yl]pentanoate (3.50 g, 8.0 mmol) in acetonitrile (150 ml) was treated with 4-toluenesulphonyl azide (2.21 g, 11.22 mmol) and N,N-diisopropylethylamine (2.1 ml, 12.08mmol) at 0° C. After 10 min., the ice-bath was removed and stirring was continued at room temperature for 2 h. The reaction mixture was diluted with ethyl acetate and washed with brine. After drying over magnesium sulphate, the solvent was evaporated in vacuo and the residue purified by chromatography on silica gel eluting with 50% ethyl acetate in hexane, then ethyl acetate to yield the title compound (2.94 g, 79%); [α]$_D$+33.6° (c 1.0 CHCl$_3$); $v_{max}$ (CH$_2$Cl$_2$) 3410, 2142, 1770, 1713, 1683 and 1515cm$^{-1}$; $\delta_H$ (CDCl$_3$) 1.59–1.78 (2H, m), 2.67–2.92 (2H, m), 3.57 and 3.64 (2H, ABq, J 15.6 Hz), 3.78 (1H, m), 3.81 (3H, s), 5.18 (2H, s), 5.24 (1H, m), 6.37 (1H, br.s, exch.), 6.59 (1H, d, J 8.2 Hz), 6.91 (2H, d, J 8.7 Hz), and 7.23–7.36 (7H, m); m/z (CI, +ve ion, ammonia) 465 (MH$^+$).

1j) 4-Methoxybenzyl (6R,7S)-7-phenylacetamido-3-(trifluoromethyl-sulphonyloxy)-1-carba-1- dethiaceph-3-em-4-carboxylate A solution of 4-methoxybenzyl 2-diazo-3-oxo-5-[(3S,4R)-3-phenyl-acetamidoazetidin-2-on-4-yl]pentanoate (2.90 g, 6.25 mmol) in chloroform (75 ml) was heated to reflux in the presence of a catalytic quantity of rhodium (II) acetate dimer. After heating for 1 h, the reaction mixture was cooled to 0° C. and treated sequentially with N,N-diisopropylethylamine (2.2 ml, 12.51 mmol) and trifluoromethanesulphonic anhydride (1.16 ml, 6.90 mmol). After stirring for 30 min. at 0° C., the mixture was concentrated in vacuo. The residue was purified by chromatography on silica gel eluting with 30, then 50% ethyl acetate in hexane yielding the title compound as an orange foam (1.80 g, 51%); [α]$_D$+24.1° (c 1.0 CHCl$_3$); $v_{max}$ (CH$_2$Cl$_2$) 3416, 1783, 1734, 1685 and 1516cm$^{-1}$; $\delta_H$ (CDCl$_3$) 1.45 (1H, m), 1.98 (1H, m), 2.56 (2H, m), 3.60 (2H, s), 3.79 (3H, s), 3.87 (1H, m), 5.13–5.32 (3H, m), 6.06 (1H, d, J 6.3 Hz), 6.86 (2H, d, J 8.7 Hz) and 7.21–7.40 (7H, m); m/z (CI, +ve ion, ammonia) 586 (MNH$_4^+$).

EXAMPLE 1

Step 1 p-Methoxybenzyl (4S,8R,9S,11R, 12S)-13-oxo-12-phenylacetamido-1-aza-6,7-benzotetracyclo[9.2.0.0$^{3,9}$.0$^{4,8}$] trideca-2,6-diene-2-carboxylate To a solution of p-methoxybenzyl (6R,7S)-3-trifluoromethanesulphonyloxy-7-phenylacetamido-1 -carba-1-dethiaceph-3-em-4-carboxylate (203 mg, 0.357 mmol) and indene (0.63 ml, 5.4 mmol) in dichloromethane (8 ml) was added a solution of 1,8-Diazabicyclo[5.4.0]undec-7-ene (DBU) (54 µl, 0.361 mmol) in dichloromethane (2 ml) dropwise over 10 min. After stirring at room temperature for 2 h the reaction mixture was chromatographed on silica gel eluting with 20% ethyl acetate in dichloromethane. Crystallisation from a mixture of ethyl acetate and dichloromethane gave the title compound as a white solid (87 mg, 46%), m.p. 241°–242° C., (Found C, 73.6; H, 5.7; N, 5.3; M$^+$, 534.2155. C$_{33}$H$_{30}$N$_2$O$_5$ requires C, 74.1; H, 5.7; N, 5.2%; M, 534.2155); $v_{max}$ (CH$_2$Cl$_2$) 1770, 1719, 1684, 1603cm$^{-1}$; $\delta_H$ (CDCl$_3$) 1.07 (1H, brq, J~11.6 Hz), 2.05 (1H, ddd, J 12.3, 6.7, 3.4), 2.96 (1H, m), 3.30, 3.23 (2H, ABq, J 17.3, 10.1, 6.1), 3.50 (1H, brt, J~6.2), 3.62 (2H, brs), 3.7 (1H, m), 3.80 (3H, s), 4.09 (1H, m), 5.22 (3H, ABq+m, J 12.0), 6.03 (1H, d, 6.1), 6.88 (2H, d, J 8.7), 7.15–7.39 (11H, m).

Step 2 p-Methoxybenzyl (4S,8R,9S,11R,12S)-12-amino-13-oxo-1-aza-6,7-benzo-tetracyclo[9.2.0.0$^{3,9}$.0$^{4,8}$]trideca-2,6-diene-2-carboxylate To a solution of the product from Step 1 (102.6 mg, 0.192 mmol) in dichloromethane (6 ml), cooled to –30° C., was added N-methylmorpholine (51.6 µl, 0.47 mmol). A solution of phosphorus pentachloride (73 mg, 0.35 mmol) in dichloromethane (2 ml) was added and the mixture stirred at –30° for 30 min. Methanol (0.47 ml) was added and the mixture allowed to warm to room temperature over 30 min. Water (0.64 ml) was then added and the mixture stirred vigorously for 1h. After concentration the residue was partitioned between water and ethyl acetate, the pH was adjusted to 7 by the addition of 1M aqueous ammonia. The organic phase was washed with water, then brine, dried (MgSO$_4$) and concentrated. The residue was purified by chromatography to give the title compound (67.8 mg, 85%) as a foam (Found: M$^+$416.1741. C$_{25}$H$_{24}$N$_2$O$_4$ requires M, 416.173); $v_{max}$ (CH$_2$Cl$_2$) 1764, 1719, 1603cm$^{-1}$;$\delta_H$ (CDCl$_3$ ) 1.37 (1H, q, J~11.6), 2.21 (1H, ddd, J 12.1, 6.5, 3.5), 3.07 (1H, m), 3.28 (2H, m), 3.62 (2H, m), 3.81 (3H, s), 4.13 (1H, m), 4.42 (1H, d, J 5.6), 5.23 (2H, ABq, J 12.0), 6.90 (2H, d, J 8.7), 7.21 (4H, m), 7.37 (2H, d, J 8.7).

Step 3 p-Methoxybenzyl (4S,8R,9S,11R,12S)-12-[2-(2-aminothiazol-4-yl)-2-(Z)-methoxyiminoacetamido]-13-oxo-1-aza-6,7- benzotetracycio [9.2.0.0$^{3,9}$.0$^{4,8}$]trideca-2,6-diene-2-carboxylate A solution of 2-(2-aminothiazol-4-yl)-2-(Z)-methoxyacetic acid (36 mg, 0.179 mmol) in dimethylformamide (DMF) (1 ml) was cooled to –30° C. Diisopropylethylamine (34.2 µl, 0.196 mmol), then methanesulphonyl chloride (15.1 µl, 0.195 mmol) were added and the mixture stirred at −30° C. for 30 min. A further portion of diisopropylethylamine (28.3 μl, 0.162 mmol) was added and the mixture was then added to a solution of the product from Step 2 (67.8 mg, 0.163 mmol) in DMF (1 ml) cooled in an ice bath. After stirring for 30 min the reaction mixture was partitioned between ethyl acetate and water. The organic phase was washed three times with water then brine. The title compound (92.2 mg, 94%) was obtained after evaporation of the solvent; $v_{max}$ (KBr) 1737, 1709, 1671cm$^{-1}$; $\delta_H$ ((CD$_3$)$_2$SO) 1.47 (1H, q, J 11.5), 2.02 (1H, m), 2.97 (1H, m), 3.24 (2H, m), 3.56 (1H, t, J 6.1), 3.71 (1H, m), 3.76 (3H, s), 3.85(3H, s), 4.06 (1H, m), 5.17 (2H, ABq, J 12.0) 5.43 (1H, dd, J 8.9, 5.4), 6.77 (1H, s), 6.95 (2H, d, J 8.7), 7.19 (4H, m), 7.26 (2H, brs), 7.39 (2H, d, J 8.7), 9.23 (1H, d, J 8.9); m/z 600(MH$^+$).

Step 4

Sodium (4S,8R,9S,11R,12S)-12-[2-(2-aminothiazol-4-yl)-2-(Z)-methoxyiminoacetamido]-13-oxo-1-aza-6,7-benzotetracyclo [9.2.0.0$^{3,9}$.0$^{4,8}$]trideca-2,6-diene-2-carboxylate The product (30 mg, 0.050 mmol) from Step 3 was suspended in anisole (1 ml) and cooled in an ice bath. Trifluoroacetic acid (1.5 ml) was added and the mixture stirred for 5 min. Toluene (2 ml) was added and the mixture evaporated to dryness. The residual solid was dissolved in tetrahydrofuran (THF) (0.3 ml), water (10 ml) was added and the mixture adjusted to pH7 by the addition of aqueous sodium bicarbonate. This mixture was chomota-graphed on HP20SS eluting with water-THF mixtures. The product (16 mg, 62%) was obtained as a freeze-dried solid; $v_{max}$ (KBr) 1745, 1664, 1618, 1530cm$^{-1}$; $\delta_H$ ((CD$_3$)$_2$SO) 1.44 (1H, q, J 11.5), 1.91 (1H, m), 2.84 (1H, m), 3.12 (1H, dd, J 17.5, 5.4), 3.27 (1H, dd, J 17.3, 10.3), 3.46 (1H, t, J 6.3), 3.60 (1H, m), 3.86 (3H, s), 4.17 (1H, m), 5.22 (1H, dd, J 8.9, 5.3), 6.75 (1H, s), 7.17 (4H, m), 7.25 (2H, brs), 9.21 (1H, d, J 8.9); m/z 480 [M−Na+2H]$^+$, 502MH$^+$.

We claim:

1. A carbacephalosporin compound of formula (I) or a salt thereof:

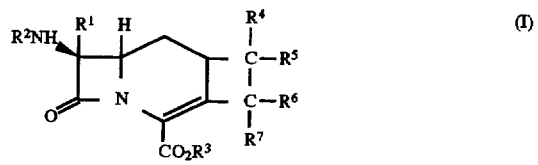

wherein $R^1$ is hydrogen, methoxy or formamido;

$R^2$ is an acyl group;

$CO_2R^3$ is a carboxy group or a carboxylate anion, or $R^3$ is a readily removable carboxy protecting group or a pharmaceutically acceptable salt-forming group or in vivo hydrolysable ester group;

$R^4$, $R^5$, $R^6$ and $R^7$ independently represent hydrogen or a substituent;

wherein $R^4$ and $R^7$ optionally are absent and replaced by a chemical bond between the two carbon atoms shown;

and wherein $R^5$ and $R^6$ optionally are linked together into a cyclic system of formula:

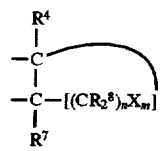

wherein X represents —O— or —NR$^8$—, wherein each $R^8$ is the same or different and independently represents hydrogen or a substituent, or two groups $R^8$ may be linked into a ring system, or any two adjacent —CR$^8_2$— units is replaced by a —CR$^8$=CR$^8$— unit, and wherein n is an integer 1 to 7, m is 0, 1, 2 or 3.

2. A compound of formula (I) as claimed in claim 1 having a formula (Ia) or pharmaceutically acceptable salts or pharmaceutically acceptable in vivo hydrolysable esters thereof:

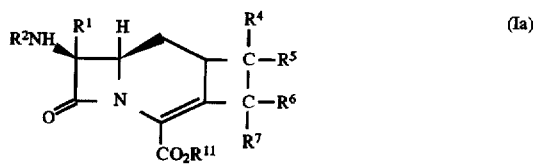

wherein $R^1$, $R^2$, $R^4$, $R^5$, $R^6$, and $R^7$ are as defined with respect to formula (I) and the group $CO_2R^{11}$ is $CO_2R^3$ where $CO_2R^3$ is a carboxy group or a carboxylate anion.

3. A compound as claimed in claim 1 or 2 in which $R^1$ is hydrogen.

4. A compound as claimed in claim 1 wherein $R^2$NH is a 2-(2-aminothiazol-4-yl)-2-(Z)-methoxy- or hydroxy-iminoacetamido group in which the amino group is in a substituted or protected form.

5. A compound of formula (I) as claimed in claim 1 having a part formula (IBi) or (IBii):

where one or both of $R^4$ and $R^5$ optionally are substituent groups other than hydrogen.

6. A compound of formula (I) as claimed in claim 1 wherein $R^5$ and $R^6$ are linked together into a cyclic ring system, $R^4$ and $R^7$ being hydrogen, and the ring system being a 5- or 6-membered ring system of part formula (IBiii), (IBiv) (IBv) or (IBvi):

-continued

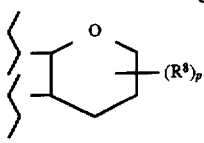
(IBiv)

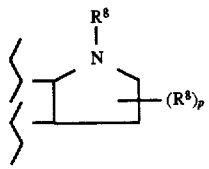
(IBv)

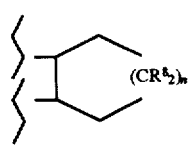
(IBvi)

where $R^8$ and n are as defined in formula (I) and p is zero or an integer up to the number of carbon atoms in the ring.

7. A compound according to claim 6 in which in part formulae (IBiii–IBvi) $R^8$ is hydrogen, and n is 1 or 2.

8. A compound of formula (I) as claimed in claim 1 wherein two groups $R^8$ are linked together to form an optionally substituted phenyl ring system in a compound of formula (I) having a part formula (IBvii):

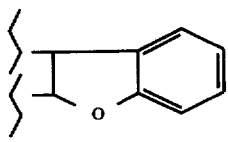
(IBvii)

wherein the phenyl ring shown in (IBvii) is optionally substituted with one or more substituents.

9. A compound of formula (IA) as claimed in claim 2, being selected from the carboxylic acids listed below, and salts and in-vivo hydrolysable esters thereof:

(4S,8R,9S,11R,12S)-12-[2-(2-aminothiazol-4-yl)-2-(Z)-methoxyiminoacetamido]-13-oxo-1-aza-6,7-benzotetracyclo [9.2.0.0$^{3,9}$.0$^{4,8}$]trideca-2,6-diene-2-carboxylic acid.

10. A process for the preparation of a compound of formula (I) as claimed in claim 1, which process comprises treating a compound of formula (II) or a salt thereof:

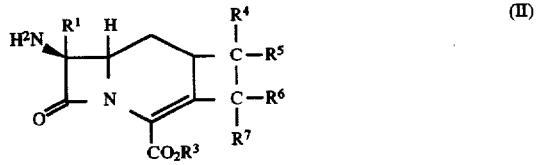
(II)

wherein $R^1$, $CO_2R^3$, $R^4$, $R^5$, $R^6$, and $R^7$ are as hereinbefore defined, wherein any reactive groups are optionally protected, and wherein the amino group is optionally substituted with a group which permits acylation to take place; with an acid of formula (III) or a N-acylating derivative thereof:

$R^2OH$ (III)

wherein $R^2$ is the acyl group as defined with respect to formula (I) and wherein any reactive groups are optionally protected; and thereafter, if necessary or desired, carrying out one or more of the following steps:

i) removing any protecting groups;
ii) converting the group $CO_2R^3$ into a different group $CO_2R^3$;
iii) convening the group $R^2$ into a different group $R^2$;
iv) converting the sulphur atom into an oxidised sulphur atom;
v) converting the product into a salt or ester.

11. A process for the preparation of a compound of formula (II) as defined in claim 10, which includes the step of reaction between a compound of formula (IV):

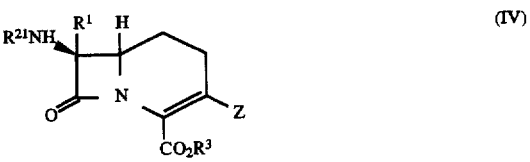
(IV)

wherein $R^1$ and $R^3$, are as defined in formula (I), $R^{21}$ is a group $R^2$ as defined in formula (I) or is an amino-protecting group or is hydrogen or a group which permits N-acylation to take place and Z is a nucleophilic leaving group, with a compound of formula (V):

(V)

wherein $R^4$, $R^5$, $R^6$ and $R^7$ are as defined with reference to formula (I); $R^4$ and $R^7$ are optionally absent and replaced by a bond to form an alkyne, and wherein $R^5$ and $R^6$ are optionally linked together into a cyclic system of formula:

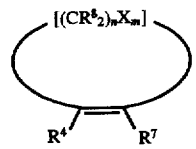

wherein X, $R^8$, n and m are as defined with respect to formula (I).

12. A pharmaceutical composition which comprises a compound of formula (Ia) or a pharmaceutically acceptable salt or in vivo hydrolysable ester thereof and a pharmaceutically acceptable carrier.

13. A compound of formula (Ia) as defined in claim 2 or a pharmaceutically acceptable salt or in vivo hydrolysable ester thereof as an active therapeutic agent.

14. A compound of formula (Ia) as defined in claim 2 or a pharmaceutically acceptable salt or in vivo hydrolysable ester thereof, useful in the treatment of bacterial infections.

15. A method of treating bacterial infections in humans and animals which comprises the administration of a therapeutically effective amount of an antibiotic compound of the formula (Ia) as defined in claim 2 or a pharmaceutically acceptable in vivo hydrolysable ester thereof.

16. A cephalosporin compound of formula (I) or salt thereof, as defined in claim 1, wherein $R^2$ is an acyl group of an antibacterially active cephalosporin.

* * * * *